(12) United States Patent
Gotteland et al.

(10) Patent No.: US 7,776,854 B2
(45) Date of Patent: *Aug. 17, 2010

(54) BENZAZOLE DERIVATIVES FOR THE TREATMENT OF SCLERODERMA

(75) Inventors: Jean-Pierre Gotteland, Beaumont (FR); Pascale Gaillard, St-Julien-en-Genevois (FR); Yolande Chvatchko, Confignon (CH)

(73) Assignee: Merck Serono SA, Coinsins, Vaud (CH)

( * ) Notice: Subject to any disclaimer, the term of this patent is extended or adjusted under 35 U.S.C. 154(b) by 814 days.

This patent is subject to a terminal disclaimer.

(21) Appl. No.: 10/496,785

(22) PCT Filed: Dec. 6, 2002

(86) PCT No.: PCT/EP02/13857

§ 371 (c)(1),
(2), (4) Date: Jan. 31, 2005

(87) PCT Pub. No.: WO03/047570

PCT Pub. Date: Jun. 12, 2003

(65) Prior Publication Data

US 2005/0119277 A1     Jun. 2, 2005

(30) Foreign Application Priority Data

Dec. 7, 2001   (EP) .................................. 01000727

(51) Int. Cl.
    *A61K 31/535*    (2006.01)
(52) U.S. Cl. .................................. 514/232.5
(58) Field of Classification Search ........................ None
    See application file for complete search history.

(56) References Cited

U.S. PATENT DOCUMENTS

2002/0111353 A1*  8/2002  Ledeboer et al. .......... 514/235.8
2003/0162794 A1*  8/2003  Halazy et al. ............... 514/256

FOREIGN PATENT DOCUMENTS

| EP | 1 110 957 | 6/2001 |
| JP | 1-180155 | 7/1989 |
| WO | 98/55110 | 12/1998 |
| WO | 01/47920 | 7/2001 |

OTHER PUBLICATIONS

Fredrick M Wigley, et al., "Novel therapy in the treatment of scleroderma", Exp. Opin. Invest. Drugs, vol. 10, No. 1, pp. 31-48 2001.
E. Carwile Leroy, "Increased collagen synthesis by scleroderma skin fibroblasts in vitro: a possible defect in the regulation or activation of the scleroderman fibroblast", The Journal of Clinical Investigation, vol. 54, No. 5, pp. 880-889 1974.
Barbara A. Hocevar, et al., "TGF-β induces fibronectin synthesis through a c-Jun N-terminal kinase-dependent, Smad4-independent pathway", The EMBO Journal, vol. 18, No. 5, pp. 1345-1356 1999.
Carol Leighton, Drugs, vol. 61, No. 3, pp. 419-427 2001.
Frank A. Anania, et al., Free Radical Biology & Medicine, vol. 30, No. 8, pp. 846-857 2001.
Colin A. Syme, et al., Am. J. Physiol. Cell Physiol. vol. 278, pp. C570-581 2000.
Naftali Kaminski, et al. PNAS, vol. 97, No. 4, pp. 1778-1783 Feb. 15, 2000.
Fredrick M Wigley, et al., Current Opinion in Anti-Inflammatory & Immunomodulatory Investigational Drugs, vol. 2, No. 4, pp. 276-292 2000.
K. Kuroda, et al., Arch. Dermatol. Res., vol. 289, pp. 567-572 1997.
John Varga, Arch. Dermatol., vol. 133, pp. 637-642 1997.
Richard P. Polisson, et al., The Journal of Rheumatology, vol. 23, No. 4, pp. 654-658 1996.
Floyd E. Fox. et al., Journal of Interferon and Cytokine Research, vol. 19, pp. 407-415 1999.
S. Bartolone, et al., Minerva Cardioangiol, vol. 47, pp. 137-143 1999.
Horst Olschewski, et al., Annals of Internal Medicine, vol. 132, No. 6, pp. 435-443 Mar. 21, 2000.
Shl-wen Xu, et al., Journal of Cardiovascular Pharmacology, vol. 31, suppl. 1, pp. S545-S547 1998.
F. H. J. Van Den Hoogen, et al., British Journal of Rheumatology, vol. 35, No. 4, pp. 364-372 1996.
Amon Nagler, at al., Transplantation , vol. 68, No. 11, pp. 1806-1809 Dec. 15, 1999.
Richard Hynes, Ann. Rev. Cell Biol., vol. 1, pp. 67-90 1985.
A.R. Kornblihtt, et al., FASEB Journal., vol. 10, pp. 248-257 1996.
Wayne A. Border, et al., The New England Journal of Medicine, vol. 331, No. 19, pp. 1286-1292 1994.
U.S. Appl. No. 10/571,291, filed Mar 9, 2006, Gaillard, et al.

* cited by examiner

*Primary Examiner*—Michael G Hartley
*Assistant Examiner*—Paul Dickinson
(74) *Attorney, Agent, or Firm*—Browdy Neimark, PLLC

(57) ABSTRACT

The present invention is related to the use of benzazole derivatives of formula (I) for the treatment and/or prevention of scleroderma and its therapeutic implications selected in the group consisting of systemic sclerosis, scleroderma-like disorders, sine scleroderma, liver cirrhosis, interstitial pulmonary fibrosis, Dupuytren's contracture, keloid and other scarring/wound healing abnormalities, postoperative adhesions and reactive fibrosis, as well as chronic heart failure, in particular after myocardial infarction.

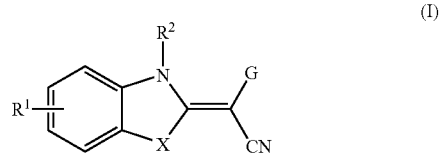

(I)

9 Claims, 4 Drawing Sheets

BENZAZOLE DERIVATIVES FOR THE TREATMENT OF SCLERODERMA

FIELD OF THE INVENTION

The present invention is related to the use of benzazole derivatives of formula (I) for the treatment of scleroderma and its therapeutic implications such as systemic sclerosis, scleroderma-like disorders or sine scleroderma for example, as well as pharmaceutical compositions containing them.

BACKGROUND OF THE INVENTION

Scleroderma is a rare disease with a stable incidence of approximately 19 cases per 1 million persons. The cause of scleroderma is unknown. However, the genetic predisposition is important. Abnormalities involve autoimmunity and alteration of endothelial cell and fibroblast function. Indeed, systemic sclerosis is probably the most severe of the auto-immune diseases with 50% mortality within 5 years of diagnosis.

Scleroderma is a disease of the connective tissue characterized by fibrosis of the skin and internal organs, leading to organ failure and death. Scleroderma has a spectrum of manifestations and a variety of therapeutic implications. It comprises localized scleroderma, systemic sclerosis, scleroderma-like disorders, and sine scleroderma. Whilst localized scleroderma is a rare dermatologic disease associated with fibrosis and manifestations limited to skin, systemic sclerosis is a multi-system disease with variable risk for internal organ involvement and variation in the extent of skin disease. Systemic sclerosis can be diffuse or limited. Limited systemic sclerosis is also called CREST (calcinosis, Raynaud's esophageal dysfunction, sclerodactyly, telangiectasiae). Systemic sclerosis comprises: scleroderma lung disease, scleroderma renal crisis, cardiac manifestations, muscular weakness including fatigue or limited CREST, gastrointestinal dysmotility and spasm, and abnormalities in the central, peripheral and autonomic nervous system. With regard to the nervous system abnormalities, carpal tunnel syndrome followed by trigeminal neuralgia are the most common. Scleroderma-like disorders are believed to be related to industrial environment exposure. In sine disease, there is internal organ involvement without skin changes.

The major manifestations of scleroderma and in particular of systemic sclerosis are inappropriate excessive collagen synthesis and deposition, endothelial dysfunction, spasm, collapse and obliteration by fibrosis. In terms of diagnosis, an important clinical parameter is skin thickening proximal to the metacarpophalangeal joints. Raynaud's phenomenon is a frequent, almost universal component of scleroderma. It is diagnosed by color changes of the skin upon cold exposure. Ischemia and skin thickening are symptoms of Raynaud's disease.

Several underlying biological processes are implicated in the initiation, severity and progression of the disease and include vascular dysfunction, endothelial cell activation and damage, leukocyte accumulation, auto-antibody production and crucially, an uncontrolled fibrotic response which may lead to death. Fibroblasts have a pivotal role in the pathogenesis of this disease. Primary fibroblasts obtained from patients with scleroderma exhibit many of the characteristic properties of the disease seen in vivo, notably increased extracellular matrix synthesis and deposition, notably of collagen and fibronectin, and altered growth factor and cytokine production such as of TGFβ and CTGF ("Increased collagen synthesis by scleroderma skin fibroblasts in vitro" *J. Clin. Invest.* 54, p. 880-89 LeRoy (1974)).

There is no curative treatment of scleroderma. Innovative but high-risk therapy proposed autologous stem cell transplantation. In particular, there are currently no treatments for scleroderma targeting the fibrotic process.

Identification of the genes associated with disease risk and scleroderma progression may lead to the development of effective strategies for intervention at various stages of the disease.

Although there is presently no cure for scleroderma, several agents or treatments are presently being used to treat scleroderma symptoms. Such anti-scleroderma agents, which may be used as combination therapy according to the invention, are summarized e.g. by Leighton C. (*Drugs* 61(3) p. 419-27 (2001)) or Wigley and Sule (*Expert opinion on Investigational Drugs* 10(1) p. 3148 (2001)), which are fully incorporated by reference herein.

A recent publication of B. A. Hocevar et al. (*The EMBO Journal* Vol. 18 No. 5 p. 1345-56 (1999)) has suggested that TGF-β-mediated gene induction would involve activation of JNK, since JNK has been shown to modulate promoters containing both AP-1 (a transcription factor, formed from a heterodimer of the products of the proto-oncogenes fos and jun and CRE sites through its phosphorylation and activation of c-Jun and ATF-2 which is a c-Jun transcription factor participating in the transcriptional activation of c-Jun gene.

c-Jun is a protein that is forming homodimers and heterodimers (with e.g. c-Fos) to produce the transactivating complex AP-1 which is required for the activation of many genes (e.g. matrix metalloproteinases) involved in the inflammatory response. The JNKs (c-Jun N-terminal Kinases) were discovered when it was found that several different stimuli such as UV light and TNF-α stimulated phosphorylation of c-Jun on specific serine residues in the N-terminus of the protein. The JNKs are also involved in relaying stress-type extramolecular signals, the ERK (extracellular regulated kinases) pathway is primarily responsible for transducing mitogenic/differentiation signals to the cell nucleus.

JNK inhibitors are disclosed in various patent applications. For instance, EP 1110957 describing benzazole derivatives in particular for the treatment or prevention of disorders associated with the abnormal expression or activity of JNK2 and/or 3, including autoimmune diseases such as Multiple Sclerosis, rheumatoid arthritis or asthma.

Recently, Anania F. A. et al. (*Free Radical Biol. Med.*, 30(8), p. 846-57 (2001)) mentioned that JNK activation appears to be critical in the signaling cascade of oxidative metabolites of chronic alcoholic related liver injury and collagen gene activation that leads to liver fibrosis before cirrhosis.

WO 9855110, Dalhousie University teaches the use of compounds such as 1-(5-oxohexyl)-3,7-dimethylxanthine (pentoxifylline) or functional derivatives thereof to reduce the effect of PDGF-induced c-Jun gene expression in order to cure fibrosis diseases in which PDGF (Platelet Derived Growth Factor) is involved and acts as a stimulant.

The use of other compounds such as [5-chloro-2(3H)benzoxazolone](chlorzoxazone) and oxazolamine as pharmacological activators of the intermediate-conductance $Ca^{2+}$-activated $K^+$ channel are described to be therapeutically beneficial in cystic fibrosis and vascular diseases (*Am. J. Physiol.*, 278(3, Pt. 1), C570-C581 (English) 2000).

SUMMARY OF THE INVENTION

The present invention is based on the finding that benzazole derivatives of formula (I)-being inhibitors of JNK (c-Jun Kinases)—are suitable for the treatment and/or prevention of scleroderma and its therapeutic applications.

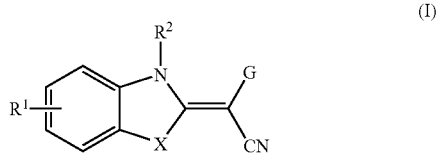

(I)

Hence, the present invention aims at providing a method for treating patients suffering from scleroderma. Furthermore, in accordance with the present invention the preparation of a medicament is presented, said medicament is useful for the treatment and/or prevention of scleroderma, in particular systemic sclerosis.

BRIEF DESCRIPTION OF THE DRAWINGS

FIG. 1 is a graphical representation, illustrating the effect of the test compound (A) on the body weight of different groups of treated mice having an induced pulmonary fibrosis. What is shown is the decrease of body weight loss following a 17 day administration (d=1 to 17) of the test compound (A) and bleomycin to mice.

FIG. 2 is a graphical representation, illustrating the decreased bleomycin-induced lung inflammation following administration of the test compound (A) to mice. What is shown is the ratio wet/dry of the examined lung lobes of mice, following a treatment by different dosages of the test compound.

FIG. 3 is a graphical representation of the histology examination of mice lungs affected by bleomycin-induced inflammation. The representation illustrates the decrease in fibrosis development within mice suffering from bleomycin-induced pulmonary fibrosis following administration of the test compound (A).

FIG. 4 is a graphical representation, illustrating the hydroxyproline quantification by a O.D. (Optical Density) count at different dosages of the test compound (A).

DESCRIPTION OF THE INVENTION

Figure 1:
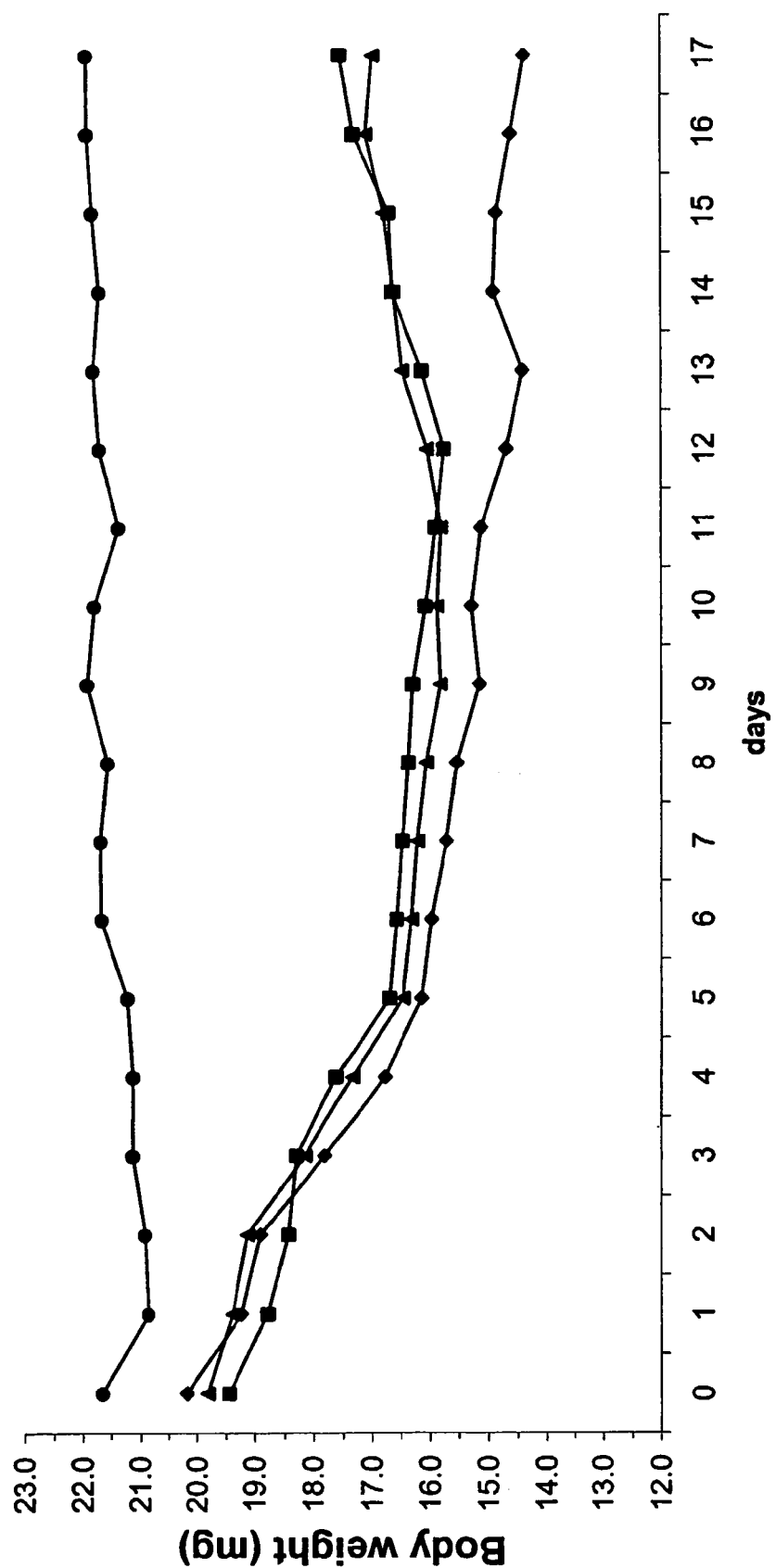
FIGS. 1 to 4 illustrate the suitability of the compounds of the present invention for the treatment of scleroderma. As an example, a test compound, designated as (A) (i.e. 1,3-benzothiazol-2-yl(2-{[4-(morpholin-4-ylmethyl)benzyl]-oxy}pyrimidin-4-yl)acetonitrile) is subjected to a bleomycin-induced lung fibrosis assay. The shown data are based on an in vivo assay, wherein a lung inflammation is induced by bleomycin. Bleomycin is an antibiotic produced by *Streptomyces verticullis*, used in the treatment of neoplasma. One of the observed side effects of the drug is the induction of pulmonary fibrosis. Bleomycin is therefore generally used in the art to artificially induce pulmonary fibrosis in animals for providing a model of pulmonary fibrosis and scleroderma (see *PNAS*, vol. 97, p. 1778-83 (2000) by Kaminski et al)

The following paragraphs provide definitions of the various chemical moieties that make up the compounds according to the invention and are intended to apply uniformly throughout the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g. phenyl) or multiple condensed rings (e.g. naphthyl). Preferred aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"Alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"Acyl" refers to the group —C(O)R where R includes "$C_1$-$C_6$-alkyl", "aryl", "heteroaryl", "$C_1$-$C_6$-alkyl aryl" or "$C_1$-$C_6$-alkyl heteroaryl".

"Acyloxy" refers to the group —OC(O)R where R includes "$C_1$-$C_6$-alkyl", "aryl", "heteroaryl", "$C_1$-$C_6$-alkyl aryl" or "$C_1$-$C_6$-alkyl heteroaryl".

"Alkoxy" refers to the group —O—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred alkoxy groups include by way of example, methoxy, ethoxy, phenoxy and the like.

"Alkoxycarbonyl" refers to the group —C(O)OR where R includes "$C_1$-$C_6$-alkyl" or "aryl" or "heteroaryl" or "$C_1$-$C_6$-alkyl aryl" or "$C_1$-$C_6$-alkyl heteroaryl".

"Aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl heteroaryl".

"Acylamino" refers to the group —NR(CO)R' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl".

"Enantiomeric excess" (ee) refers to the products that are obtained by an essentially enantiomeric synthesis or a synthesis comprising an enantioselective step, whereby a surplus of one enantiomer in the order of at least about 52% ee is yielded.

"Halogen" refers to fluoro, chloro, bromo and iodo atoms.

"Sulfonyl" refers to group "—$SO_2$—R" wherein R is selected from H, "aryl", "heteroaryl", "$C_1$-$C_6$-alkyl", "$C_1$-$C_6$-alkyl" substituted with halogens e.g. an —$SO_2$—$CF_3$ group, "$C_1$-$C_6$-alkyl aryl" or "$C_1$-$C_6$-alkyl heteroaryl".

"Sulfoxy" refers to a group "—S(O)—R" wherein R is selected from H, "$C_1$-$C_6$-alkyl", "$C_1$-$C_6$-alkyl" substituted with halogens e.g. an —SO—$CF_3$ group, "aryl", "heteroaryl", "$C_1$-$C_6$-alkyl aryl" or "$C_1$-$C_6$-alkyl heteroaryl".

"Thioalkoxy" refers to groups —S—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred thioalkoxy groups include thiomethoxy, thioethoxy, and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$-$C_6$-alkyl", "$C_1$-$C_6$-alkyl aryl", "$C_1$-$C_6$- alkyl heteroaryl", "$C_2$-$C_6$-alkenyl", "$C_2$-$C_6$-alkynyl", primary, secondary or tertiary amino groups or quarter-nary ammonium moieties, "acyl", "acyloxy", "acylamino", "aminocarbonyl", "alkoxycarbonyl", "aryl", "heteroaryl", carboxyl, cyano, halogen, hydroxy, mercapto, nitro, sulfoxy, sulfonyl, alkoxy, thioalkoxy, trihalomethyl and the like. Alternatively said substitution could also comprise situations where neighboring substituents have undergone ring closure, notably when viccinal functional substituents are involved, thus forming e.g. lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-identified compounds of formula I that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and polygalacturonic acid. Said compounds can also be administered as pharmaceutically acceptable quaternary salts known by a person skilled in the art, which specifically include the quarternary ammonium salt of the formula —NR,R',R"$^+$Z$^-$, wherein R, R', R" is independently hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate). Sample based-addition salts include those derived from sodium, potassium, ammonium, and quaternary ammonium hydroxide, such as for example tetramethylammonium hydroxide.

"Pharmaceutically active derivative" refers to any compound that upon administration to the recipient, is capable of providing directly or indirectly, the activity disclosed herein.

"Treatment" refers to any attenuation, reduction, or partial, substantial or complete blockage of disease formation, development, progression or of the formation, development or progression of any one or several or all of the symptoms of the disease.

"Scleroderma" refers to scleroderma in any classification and definition, as well as one or more of the symptoms of scleroderma, as described in detail in the introduction. This term further relates to the diseases known to be associated with scleroderma, such as the ones described by Smith (*Textbook of the Autoimmune Diseases*, edited by Lahita, Chiorazzi and Reeves, Lippincott Williams & Wilkins, Philadelphia (2000)). Said term preferably relates to localized, systemic, limited and diffuse scleroderma as well as overlap syndromes:

Localized scleroderma primarily affects the skin, but may also affect the underlying muscles and bones. However, it does not affect internal organs. Localized scleroderma is relatively mild and may be related to systemic scleroderma in terms of similar superficial symptoms, such as the appearance of skin biopsy under the microscope.

Systemic scleroderma comprises several types of symptoms or groups of symptoms, such as CREST, limited and diffuse. Systemic scleroderma is also known as systemic sclerosis. It may also referred to as progressive systemic sclerosis. Systemic scleroderma e.g. affects the skin, blood vessels, and/or internal organs. When it affects the skin, it may cause the skin to harden, most commonly on the hands and/or face. When it affects the blood vessels, it can cause Raynaud's disease. The most serious forms of systemic sclerosis affect the internal organs, and may cause disability or even death. Among others, systemic sclerosis comprises: scleroderma lung disease, scleroderma renal crisis, cardiac manifestations, muscular weakness including fatigue or limited CREST, gastrointestinal dysmotility and spasm, and abnormalities in the central, peripheral and autonomic nervous system. With regard to the nervous system anormalities, carpal tunnel syndrome followed by trigeminal neuralgia are the most common.

Limited scleroderma may be limited to the hands, although the face and neck may also be involved.

Diffuse scleroderma comprises skin tightening and also occurs above the wrists (or elbows). There are several subcategories of diffuse systemic sclerosis, such as "sine scleroderma" where there is internal organ fibrosis, but no skin tightening; and familial progressive systemic sclerosis, a rare form which occurs in families.

Scleroderma further refers to fibrotic diseases such as liver cirrhosis, interstitial pulmonary fibrosis, Dupuytren's contracture, keloid and other scarring/wound healing abnormalities, postoperative adhesions and reactive fibrosis, as well as chronic heart failure, in particular after myocardial infarction.

Overlap syndromes are referred to if a scleroderma patient also has other autoimmune disease (such as lupus, rheumatoid arthritis, etc.), as e.g. in diffuse scleroderma in overlap with lupus. Scleroderma symptoms can also be a part of mixed connective tissue disease (MCTD), or Undifferentiated Connective Tissue Disease (UCTD).

In accordance with the present invention it has been found that benzazole compounds according to Formula I,

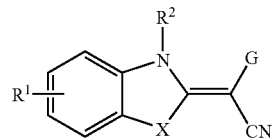

as well as its tautomers, geometrical isomers, its optically active forms as enantiomers, diastereomers and its racemate forms, as well as pharmaceutically acceptable salts thereof, are useful for the preparation of a medicament for the treatment and/or prevention of scleroderma and its therapeutic implications.

Said therapeutic implications selected in the group consisting of systemic sclerosis, scleroderma-like disorders, sine scleroderma, scleroderma lung disease, scleroderma renal crisis, cardiac manifestations, muscular weakness including fatigue or limited CREST, gastrointestinal dysmotility and spasm, and abnormalities in the central, peripheral and autonomic nervous system particularly carpal tunnel syndrome and trigeminal neuralgia, liver cirrhosis, interstitial pulmonary fibrosis, Dupuytren's contracture, keloid and other scarring/wound healing abnormalities, postoperative adhesions and reactive fibrosis, as well as chronic heart failure, in particular after myocardial infarction In Formula I:

X is O, S or NR$^0$, with R$^0$ being H or an unsubstituted or substituted $C_1$-$C_6$ alkyl. Most preferred is X=S thus yielding benzothiazoles.

G is an unsubstituted or substituted or fused pyrimidinyl group.

R¹ is selected from the group comprising or consisting of hydrogen, unsubstituted or substituted $C_1$-$C_6$-alkoxy, unsubstituted or substituted $C_1$-$C_6$-thioalkoxy, unsubstituted or substituted $C_1$-$C_6$-alkyl, unsubstituted or substituted $C_2$-$C_6$-alkenyl, unsubstituted or substituted $C_2$-$C_6$-alkynyl, primary, secondary or tertiary amino groups, aminoacyl, aminocarbonyl, unsubstituted or substituted $C_1$-$C_6$ alkoxycarbonyl, unsubstituted or substituted aryl, unsubstituted or substituted heteroaryl, carboxyl, cyano, halogen, hydroxy, nitro, sulfoxy, sulfonyl, sulfonamide, unsubstituted or substituted hydrazides.

Most preferred substituents R¹ are hydrogen, halogen, $C_1$-$C_6$-alkyl and $C_1$-$C_6$ alkoxy groups.

R² is selected from the group comprising or consisting of hydrogen, unsubstituted or substituted $C_1$-$C_6$-alkyl, unsubstituted or substituted $C_2$-$C_6$-alkenyl, unsubstituted or substituted $C_2$-$C_6$-alkyl, unsubstituted or substituted $C_1$-$C_6$-alkyl-aryl, unsubstituted or substituted aryl or heteroaryl, unsubstituted or substituted $C_1$-$C_6$-alkyl-heteroaryl, —C(O)—OR³, —C(O)—R³, —C(O)—NR³R³', —(SO₂)R³, whereby R³ and R³' are independently selected from the group comprising or consisting of hydrogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted aryl, unsubstituted or substituted heteroaryl, unsubstituted or substituted $C_1$-$C_6$-alkyl aryl, unsubstituted or substituted $C_1$-$C_6$-alkyl heteroaryl, R³ and R³' being independently selected from the group comprising or consisting of hydrogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted aryl, unsubstituted or substituted heteroaryl, unsubstituted or substituted $C_1$-$C_6$-alkyl aryl, unsubstituted or substituted $C_1$-$C_6$-alkyl heteroaryl.

Preferred substituents R² are hydrogen, unsubstituted or substituted $C_1$-$C_6$ alkyl, unsubstituted or substituted $C_1$-$C_6$ alkylaryl or $C_1$-$C_6$ alkylheteroaryl group, —C(O)—R³, —C(O)—NR³R³', —(SO₂)R³, whereby R³ and R³' are as above defined. More preferred substituents R² are hydrogen and $C_1$-$C_6$-alkyl groups, whereby R²=H is the most preferred embodiment. Preferred R³ and R³' are hydrogen, $C_1$-$C_6$ alkyl, aryl, heteroaryl, $C_1$-$C_6$-alkyl aryl, $C_1$-$C_6$-alkyl heteroaryl. Most preferred R³ and R³' is hydrogen or $C_1$-$C_6$ alkyl.

The tautomers mentioned herein are only those wherein R² and/or R⁰ are hydrogen and which display the formula II, more specifically formula IIa and IIb. Said tautomers undergo transformation in solution and an equilibrium between the benzazoles of formula Ia and Ib is established with those of formula IIa and IIb.

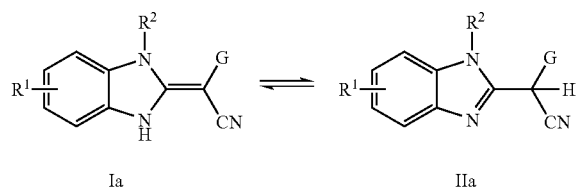

Ia          IIa

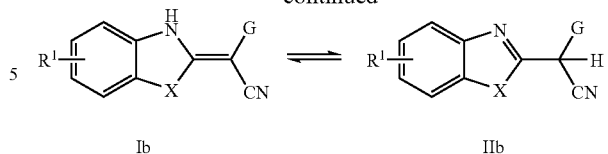

Ib          IIb

Said tautomers are comprised by the present application.

Basically, all of the above mentioned aryl or heteroaryl substituents could optionally be further substituted by at least one of the groups selected from substituted or unsubstituted $C_1$-$C_6$-alkyl, like trihalomethyl, substituted or unsubstituted $C_1$-$C_6$-alkoxy, acetoxy, substituted or unsubstituted $C_2$-$C_6$-alkenyl, substituted or unsubstituted $C_2$-$C_6$-alkynyl, amino, aminoacyl, aminocarbonyl, $C_1$-$C_6$-alkoxycarbonyl, aryl, carboxyl, cyano, halogen, hydroxy, nitro, sulfonyl, sulfoxy, $C_1$-$C_6$-thioalkoxy. Preferably said aryl or heteroaryl groups are substituted by halogen, hydroxy, nitro, sulfonyl, e.g. a trifluoromethylsulfonyl group. Particularly preferred benzazole derivatives are those wherein G is an unsubstituted or substituted pyrimidinyl group which are linked to the benzazole acetate scaffold via the position 4

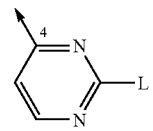

wherein L is selected from the group comprising or consisting of hydrogen, unsubstituted or substituted $C_1$-$C_6$ alkyl, unsubstituted or substituted $C_1$-$C_6$ alkoxy, unsubstituted or substituted $C_1$-$C_6$ thioalkoxy, unsubstituted or substituted $C_2$-$C_6$ alkenyl, unsubstituted or substituted $C_2$-$C_6$ alkynyl, primary, secondary or tertiary amino groups, aminoacyl, aminocarbonyl, amino-($C_1$-$C_{10}$)alkyl, amino-unsubstituted or substituted ($C_1$-$C_{10}$)-alkyl-aryl, amino-unsubstituted or substituted ($C_1$-$C_{10}$)alkyl-heteroaryl, unsubstituted or substituted $C_1$-$C_6$ alkoxycarbonyl, carboxyl, cyano, halogen, hydroxy, nitro, sulfoxy, sulfonyl, unsubstituted or substituted aryl, unsubstituted or substituted heteroaryl, unsubstituted or substituted 3-8 membered cycloalkyl, optionally containing at least one heteroatom selected from N, O, S, and unsubstituted or substituted hydrazido groups.

Particularly preferred benzazole derivatives are those wherein L is a substituted or unsubstituted ($C_1$-$C_{10}$)-alkyl group.

Further particularly preferred benzazole derivatives are those wherein L is a group —N(Rᵃ, Rᵇ) or —ORᵃ, with Rᵃ and Rᵇ being each independently selected from the group consisting of H, unsubstituted or substituted ($C_1$-$C_{10}$)-alkyl, unsubstituted or substituted $C_1$-$C_6$ alkyl-aryl, unsubstituted or substituted $C_1$-$C_6$-alkyl-heteroaryl, unsubstituted or substituted aryl or heteroaryl and unsubstituted or substituted 4-8 membered saturated or unsaturated cyclo-alkyl.

Pursuant to a particularly preferred embodiment according to formula I L is selected from

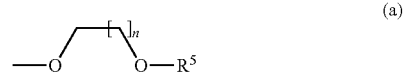

(a)

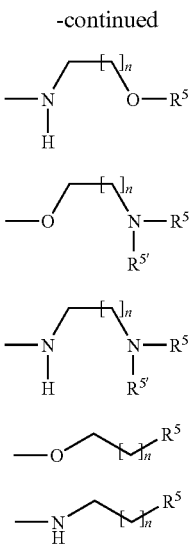

wherein n is 1 to 10, preferably 1 to 6, while X is preferably S, R¹ is H and R² is H.

R⁵ and R⁵' are independently selected from each other from the group consisting of H, substituted or unsubstituted $C_1$-$C_{10}$ allyl, substituted or unsubstituted aryl or heteroaryl, substituted or unsubstituted $C_1$-$C_6$ alkyl-aryl and substituted or unsubstituted $C_1$-$C_6$-alkyl-heteroaryl. Most preferred R⁵' is an unsubstituted or substituted imidazolyl.

The most preferred benzazole derivatives according to formula I are benzothiazole acetonitrile derivatives of the formula Ib and/or its tautomers of formula IIb

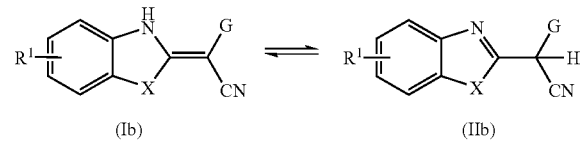

wherein X is S, R¹ is H or $C_1$-$C_6$ alkyl and R² is H, while G is a pyrimidinyl group of the formula

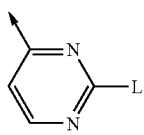

with L being either

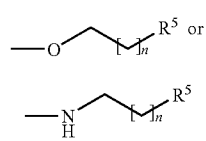

wherein n is 0, 1 or 2 and R⁵ is an aryl or heteroaryl, in particular substituted or unsubstituted phenyl, substituted or unsubstituted pyridyl, substituted or unsubstituted imidazolyl.

Specific examples of particularly useful compounds of formula I include the following:

1,3-benzothiazol-2-yl(2-chloro-4-pyrimidinyl)acetonitrile
1,3-benzothiazol-2-yl(2,6-dimethoxy-4-pyrimidinyl)acetonitrile
1,3-benzothiazol-2-yl(2-chloro-6-methyl-4-pyrimidinyl)acetonitrile
1,3-benzothiazol-2-yl[2-(methylsulfanyl)-4-pyrimidinyl]acetonitrile
1,3-benzothiazol-2-yl {6-chloro-5-nitro-4-pyrimidinyl}acetonitrile
1,3-benzothiazol-2-yl(hydroxy-4--4-pyrimidinyl)acetonitrile
1,3-benzothiazol-2-yl(2-phenyl-4-quinazolinyl)acetonitrile
(2-chloropyrimidin-4-yl)[5-(trifluoromethyl)-1,3-benzothiazol-2-yl]acetonitrile
(2E)-(2-chloro-4-pyrimidinyl)(3-methyl-1,3-benzothiazol-2(3H)-ylidene)ethanenitrile
1,3-benzothiazol-2-yl(2-([2-(1H-imidazol-5-yl)ethyl]amino)-4-pyrimidinyl)acetonitrile
1,3-benzothiazol-2-yl[2-(1-piperazinyl)-4-pyrimidinyl]acetonitrile
1,3-benzothiazol-2-yl[2-(4-benzyl-1-piperidinyl)-4-pyrimidinyl]acetonitrile
1,3-benzothiazol-2-yl[2-(4-methyl-1-piperazinyl)-4-pyrimidinyl]acetonitrile
1,3-benzothiazol-2-yl[2-(4-morpholinyl)-4-pyrimidinyl]acetonitrile
1,3-benzothiazol-2-yl[2-(methylamino)-4-pyridinyl]acetonitrile
1,3-benzothiazol-2-yl(2-{4-[2-(4-morpholinyl)ethyl]-1-piperazinyl}-4-pyrimidinyl)-acetonitrile
1,3-benzothiazol-2-yl {2-[4-(benzyloxy)-1-piperidinyl]4-pyrimidinyl}acetonitrile
1,3-benzothiazol-2-yl[2-(4-hydroxy-1-piperidinyl)-4-pyrimidinyl]acetonitrile
1,3-benzothiazol-2-yl(2-hydrazino-4-pyrimidinyl)acetonitrile
1,3-benzothiazol-2-yl(2-{[2-(dimethylamino)ethyl]amino}-4-pyrimidinyl)acetonitrile
1,3-benzothiazol-2-yl[2-(dimethylamino)-4-pyrimidinyl]acetonitrile
1,3-benzothiazol-2-yl {2-[(2-methoxyethyl)amino]4-pyrimidinyl}acetonitrile
1,3-benzothiazol-2-yl {2-[(2-hydroxyethyl)amino]4-pyrimidinyl}acetonitrile
1,3-benzothiazol-2-yl[2-(propylamino)-4-pyrimidinyl]acetonitrile
1,3-benzothiazol-2-yl(2-{[3-(1H-imidazol-1-yl)propyl]amino}-4-pyrimidinyl)acetonitrile
1,3-benzothiazol-2-yl[2-(1-pyrrolidinyl)-4-pyrimidinyl]acetonitrile
1,3-benzothiazol-2-yl {2-[(2-phenylethyl)amino]4-pyrimidinyl}acetonitrile
1,3-benzothiazol-2-yl(2-{[2-(2-pyridinyl)ethyl]amino}-4-pyrimidinyl)acetonitrile
1,3-benzothiazol-2-yl {2-[(2-pyridinylmethyl)amino]4-pyrimidinyl}acetonitrile
1,3-benzothiazol-2-yl {2-[4-(1H-1,2,3-benzotriazol-1-yl)-1-piperidinyl]4-pyrimidinyl}acetonitrile
1,3-benzothiazol-2-yl {2-[4-(2-pyrazinyl)-1-piperazinyl]-4-pyrimidinyl}acetonitrile 1,3-benzothiazol-2-yl {2-[4-(2-pyrimidinyl)-1-piperazinyl] 4-pyrimidinyl}acetonitrile
1,3-benzothiazol-2-yl(2-{[2-(3-pyridinyl)ethyl]amino}-4-pyrimidinyl)acetonitrile
1,3-benzothiazol-2-yl(5-bromo-2-{[2-(dimethylamino) ethyl]amino}-4-pyrimidinyl)-acetonitrile
1,3-benzothiazol-2-yl{2-[(2-morpholin-4-ylethyl)amino] pyrimidin-4-yl}acetonitrile
1,3-benzothiazol-2-yl[2-(4-{3-[(trifluoromethyl)sulfonyl] anilino}piperidin-1-yl)pyrimidin-4-yl]acetonitrile
1,3-benzothiazol-2-yl(2-{[3-(2-oxopyrrolidin-1-yl)propyl] amino}pyrimidin-4-yl)-acetonitrile
1,3-benzothiazol-2-yl(2-{methyl[3-(methylamino)propyl] amino}pyrimidin-4-yl)acetonitrile
1,3-benzothiazol-2-yl(2-{[3-(4-methylpiperazin-1-yl)propyl]amino}pyrimidin-4-yl)-acetonitrile
1,3-benzothiazol-2-yl{2-[(3-morpholin-4-ylpropyl)amino] pyrimidin-4-yl}acetonitrile
1,3-benzothiazol-2-yl(2-{[2-(1-methyl-1H-imidazol-4-yl) ethyl]amino}pyrimidin-4-yl)acetonitrile
1,3-benzothiazol-2-yl(2-{([2-(1H-indol-3-yl)ethyl] amino}pyrimidin-4-yl)acetonitrile
1,3-benzothiazol-2-yl(2-{[2-(4-hydroxyphenyl)ethyl] amino}pyrimidin-4-yl)acetonitrile
tert-butyl({4-[1,3-benzothiazol-2-yl(cyano)methyl]pyrimidin-2-yl}amino)acetate
{2-[(3-aminopropyl)amino]pyrimidin-yl)}(1,3-benzothiazol-2-yl)acetonitrile
{2-[(2-aminoethyl)amino]pyrimidin-4-yl}(1,3-benzothiazol-2-yl)acetonitrile
1,3-benzothiazol-2-yl(2-{[3-(dimethylamino)propyl] amino}pyrimidin-4-yl)acetonitrile
1,3-benzothiazol-2-yl {2-[(2-piperidin-1-ylethyl)amino]pyrimidin-4-yl}acetonitrile
1,3-benzothiazol-2-yl(2-{[2-(1-methyl-1H-imidazol-5-yl) ethyl]amino}pyrimidin-4-yl)acetonitrile
1,3-benzothiazol-2-yl[2-(benzylamino)pyrimidin-4-yl]acetonitrile
isopropyl 3-({4-[1,3-benzothiazol-2-yl(cyano)methyl]pyrimidin-2-yl}amino)propanoate
1,3-benzothiazol-2-yl {2-[(3-hydroxypropyl)amino]pyrimidin-4-yl}acetonitrile
1,3-benzothiazol-2-yl {2-[(pyridin-3-ylmethyl)amino]pyrimidin-4-yl}acetonitrile
(2-aminopyrimidin-4-yl)(1,3-benzothiazol-2-yl)acetonitrile
1,3-benzothiazol-2-yl {2-[(pyridin-4-ylmethyl)amino]pyrimidin-4-yl}acetonitrile
tert-butyl 4-[2-({4-[1,3-benzothiazol-2-yl(cyano)methyl]pyrimidin-2-yl}amino)-ethyl]phenylcarbamate
(2-{[2-(4-aminophenyl)ethyl]amino}pyrimidin-4-yl)(1,3-benzothiazol-2-yl)acetonitrile
1,3-benzothiazol-2-yl(2-{[2-(3,4-dimethoxyphenyl)ethyl] amino}pyrimidin-4-yl)acetonitrile
1,3-benzothiazol-2-yl(2-{[2-(3-methoxyphenyl)ethyl] amino}pyrimidin-4-yl)acetonitrile
1,3-benzothiazol-2-yl(2-{[2-(2-fluorophenyl)ethyl] amino}pyrimidin-4-yl)acetonitrile
1,3-benzothiazol-2-yl[2-({2-[3-(trifluoromethyl)phenyl] ethyl}amino)pyrimidin-4-yl]acetonitrile
1,3-benzothiazol-2-yl {2-[(2-hydroxy-2-phenylethyl)amino] pyrimidin-4-yl}acetonitrile
1,3-benzothiazol-2-yl {2-[(2-{[3-(trifluoromethyl)pyridin-2-yl]amino}ethyl)amino]-pyrimidin-4-yl}acetonitrile
1,3-benzothiazol-2-yl(2-{[2-(3-chlorophenyl)ethyl] amino}pyrimidin-4-yl)acetonitrile
1,3-benzothiazol-2-yl(2-{[2-(3,4-dichlorophenyl)ethyl] amino}pyrimidin-4-yl)acetonitrile
1,3-benzothiazol-2-yl(2-{[2-(4-methoxyphenyl)ethyl] amino}pyrimidin-4-yl)acetonitrile
1,3-benzothiazol-2-yl(2-{[2-(4-methylphenyl)ethyl] amino}pyrimidin-4-yl)acetonitrile
1,3-benzothiazol-2-yl(2-{[2-(3-fluorophenyl)ethyl] amino}pyrimidin-4-yl)acetonitrile
1,3-benzothiazol-2-yl(2-{[2-(4-phenoxyphenyl)ethyl] amino}pyrimidin-4-yl)acetonitrile
1,3-benzothiazol-2-yl(2-{([2-(2-phenoxyphenyl)ethyl] amino}pyrimidin-4-yl)acetonitrile
1,3-benzothiazol-2-yl(2-{[2-(4-bromophenyl)ethyl] amino}pyrimidin-4-yl)acetonitrile
1,3-benzothiazol-2-yl(2-{[2-(4-fluorophenyl)ethyl] amino}pyrimidin-4-yl)acetonitrile
1,3-benzothiazol-2-yl {2-[(2-[1,1'-biphenyl]4-ylethyl) amino]pyrimidin-4-yl}acetonitrile
1,3-benzothiazol-2-yl {2-[(2-{4-[hydroxy(oxido)amino] phenyl}ethyl)amino]pyrimidin-4-yl}acetonitrile
1,3-benzothiazol-2-yl(2-{[2-(1H-1,2,4-triazol-1-yl)ethyl] amino}pyrimidin-4-yl)acetonitrile
1,3-benzothiazol-2-yl(2-{[3-(1H-pyrazol-1-yl)propyl] amino}pyrimidin-4-yl)acetonitrile
4-[2-({4-[1,3-benzothiazol-2-yl(cyano)methyl]pyrimidin-2-yl}amino)ethyl]benzene-sulfonamide
{2-[(2-pyridin-3-ylethyl)amino]pyrimidin-4-yl][5-(trifluoromethyl)-1,3-benzothiazol-2-yl]acetonitrile
1,3-benzothiazol-2-yl {2-[(1H-tetraazol-5-ylmethyl)amino] pyrimidin-4-yl}acetonitrile
1,3-benzothiazol-2-yl[2-(benzyloxy)pyrimidin-4-yl]acetonitrile
1,3-benzothiazol-2-yl {2-[(4-pyridin-3-ylbenzyl)oxy]pyrimidin-4-yl}acetonitrile
1,3-benzothiazol-2-yl[2-(pyridin-4-ylmethoxy)pyrimidin-4-yl]acetonitrile
1,3-benzothiazol-2-yl[2-(pyridin-2-ylmethoxy)pyridin-4-yl]acetonitrile
1,3-benzothiazol-2-yl[2-(3-pyridin-2-ylpropoxy)pyrimidin-4-yl]acetonitrile
1,3-benzothiazol-2-yl {2-[(4-methoxybenzyl)oxy]pyrimidin-4-yl}acetonitrile
1,3-benzothiazol-2-yl[2-(pyridin-3-ylmethoxy)pyrimidin-4-yl]acetonitrile
1,3-benzothiazol-2-yl {2-[2-(4-methoxyphenyl)ethoxy]pyrimidin-4-yl}acetonitrile
1,3-benzothiazol-2-yl[2-([1,1'-biphenyl]-3-ylmethoxy)pyrimidin-4-yl]acetonitrile
1,3-benzothiazol-2-yl {2-[(3,4,5-trimethoxybenzyl)oxy]pyrimidin-4-yl}acetonitrile
1,3-benzothiazol-2-yl {2-[(3,4-dichlorobenzyl)oxy]pyrimidin-4-yl}acetonitrile
1,3-benzothiazol-2-yl[2-({3-[(dimethylamino)methyl] benzyl}oxy)pyrimidin-4-yl]acetonitrile
1,3-benzothiazol-2-yl {2-[(1-oxidopyridin-3-yl)methoxy] pyrimidinyl}acetonitrile
1,3-benzothiazol-2-yl(2-{[4-(morpholin-4-ylmethyl)benzyl] oxy}pyrimidin-4-yl)acetonitrile
1,3-benzothiazol-2-yl {2-[(4-pyridin-2-ylbenzyl)oxy]pyrimidin-4-yl}acetonitrile
1,3-benzothiazol-2-yl(2-{[4-(piperidin-1-ylmethyl)benzyl] oxy}pyrimidin-4-yl)acetonitrile
1,3-benzothiazol-2-yl[2-(4-methoxyphenoxy)pyrimidin-4-yl]acetonitrile
1,3-benzothiazol-2-yl[2-(4-butoxyphenoxy)pyrimidin-4-yl] acetonitrile
{2-[4-(4-acetylpiperazin-1-yl)phenoxy]pyrimidin-4-yl}(1,3-benzothiazol-2-yl)acetonitrile

[2-(4-methoxyphenoxy)pyrimidin-4-yl][5-(trifluoromethyl)-1,3-benzothiazol-2-yl]acetonitrile
1,3-benzothiazol-2-yl(pyrimidin-4-yl)acetonitrile
N-[2-({4-[1,3-benzothiazol-2-yl(cyano)methyl]pyrimidin-2-yl}amino)ethyl]-4-chlorobenzamide
1,3-benzothiazol-2-yl(2-methoxy-4-pyrimidinyl)acetonitrile A particularly preferred benzothiazole derivative is 1,3-benzothiazol-2-yl(2-{[4-(morpholin-4-ylmethyl)benzyl]oxy}pyrimidin-4-yl)acetonitrile.

Furthermore, the benzothiazole derivative may be used together with a further anti-scleroderma agent. For this purpose, a preferred anti-scleroderma agent is selected from the group consisting of ACE inhibitors, calcium channel blockers, proton pump inhibitors, NSAIDs, COX-inhibitors, corticosteroids, tetracycline, pentoxifylline, bucillamine, geranygeranyl transferase inhibitors, rotterlin, prolyl-4-hydroxylase inhibitors, c-proteinase inhibitors, lysyl-oxidase inhibitors, relaxin, halofuginone, prostaglandins, prostacyclins, endothelin-1, nitric oxide, angiotensin II inhibitors and anti-oxidants.

A detailed description of methods for preparing compounds of Formula (I) is given in WO 01/47920 (PCT/EP00/13006).

As an example, the preparation of benzazole derivatives according to formula IV' may be performed as follows:

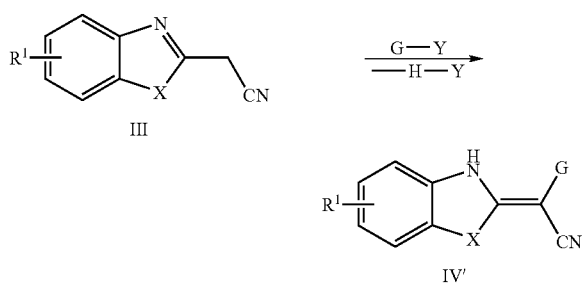

The intermediate compound IV' may be transformed in the following way:

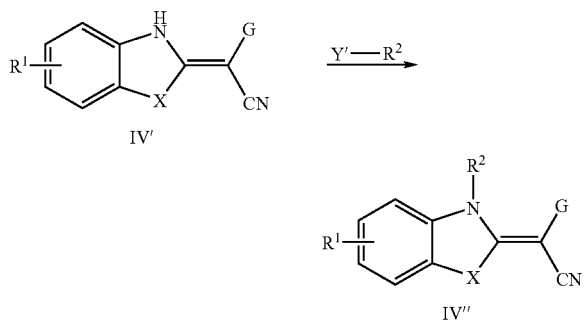

Y is a suitable leaving group.

When employed as pharmaceuticals, the benzazole derivatives of the present invention are typically administered in the form of a pharmaceutical composition. Hence, pharmaceutical compositions comprising a compound of formula I and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the benzazole derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, intrathecal, intraperitoneal and intranasal. Depending on the intended route of delivery, the compounds are preferably formulated as either injectable, topical or oral compositions. The compositions for oral administration may take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the is desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the benzazole compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the benzazole derivatives of formula I in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 8 of *Remington's Pharmaceutical Sciences, 20th* Edition, 2000, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences*.

In the following the present invention shall be illustrated by means of some exemplary biological assays as well as the synthesis of one test compound, i.e. of 1,3-benzothiazol-2-yl (2-{[4-(morpholin-4-ylmethyl)benzyl]oxy}pyrimidin-4-yl) acetonitrile (TFA). Said examples are not to be construed as limiting the scope of the present invention.

EXAMPLES

Example 1

Preparation of 1,3-benzothiazol-2-yl(2-{[4-(morpholin-4-ylmethyl)benzyl]-oxy}pyrimidin-4-yl)acetonitrile (TFA) (Test Compound (A))

Step 1: Synthesis of methyl 4-bromomethylbenzoate

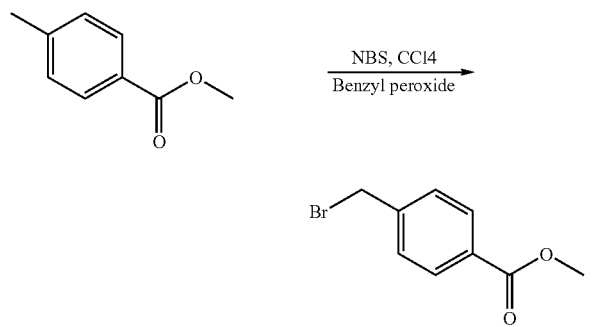

To a suspension of 150 g of methyl p-toluate and 195.5 g of NBS in CCl$_4$ (1.67 L) under N$_2$ at 50° C. was added portion wise over 30 min, solid benzoyl peroxide (5.0 g). There was no exothermic reaction observed. After heating for 2 hours at 50° C., the yellow solution was heated at 65° C. for 6 hrs. There was still some unreacted starting material. The suspension was stirred overnight at 65° C. After cooling to room temperature (r.t), the precipitate formed was filtered off and washed with 150 mL of CCl$_4$ and the filtrate was concentrated to afford a yellow oil that solidified on standing. The title compound, containing a small fraction of starting material was used in the next step without further purification.

Step 2: Synthesis of methyl 4-morpholinomethylbenzoate

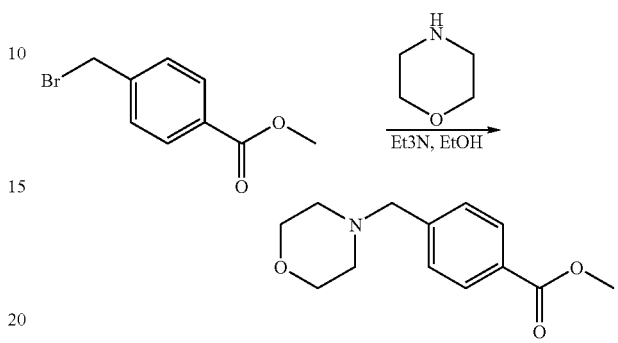

To a solution of 66.6 g of morpholine and 269 mL of triethylamine in 1.5 L of abs. EtOH under N$_2$ at 0° C. was added dropwise over 30 min a solution of methyl 4-bromomethylbenzoate (from the previous reaction) in 450 mL of abs. EtOH. The resulting solution was stirred at 0° C. for 2 hours at which point the reaction was slowly warmed up to r.t over 4 hours and stirred at r.t overnight. The HPLC showed no unreacted methyl 4-bromomethylbenzoate but the remaining methyl p-toluate from the previous reaction. The solvent was removed under reduced pressure and the residue was taken up in 2 L of 1.5 N HCl. The acidic phase was washed with 3×350 mL diethyl ether and then with 1×350 mL EtOAc then neutralized to pH 7 with NaOH and then to pH 7.5 with 10% NaHCO$_3$ in water. The product was then extracted with 3×700 mL of EtOAc. The organic phase was dried over anhydrous Na$_2$SO$_4$, filtered, and concentrated under reduce pressure, affording an orange oil. The excess EtOAc was removed by toluene distillation. The title compound was used in the next step without ether purification.

Step 3: Synthesis of 4-morpholinomethylbenzyl Alcohol

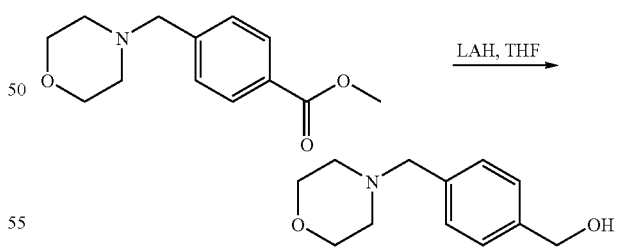

To a suspension of 33.9 g of LAH in 1633 mL of dry THF under N$_2$ at 0° C. was added drop wise a solution of methyl 4-methylmorpholinobenzoate (from the previous reaction) in 233 mL of dry THF over 30 min. The temperature remained under 15° C. during the addition. The reaction was allowed to stir at r.t overnight. It was then cooled to 0° C. and quenched with 220 mL 10% NaOH. The NaOH was added drop wise (over 30 min) keeping the temperature below 10° C. It was then warmed to r.t and stirred for 2 hours. The precipitate formed was filtered off and washed with 200 mL of THF. The filtrate was concentrated affording a white solid that was taken up in EtOAc (1 L) and heated at 65° C. for 45 min and then cooled to r.t. The EtOAc solution was washed with 1×250 mL 15% brine. Then 700 mL of the solvent was removed to give a suspension of the product and 300 mL of hexane. The solution was cooled to 4° C. and held for 12 hours. The crystals were filtered off and washed with a cold 1:1 mixture of EtOAc/:hexane (200 mL) then dried at 40° C. under vacuum overnight, affording 107.5 g (52% yield from methyl p-toluate) of as white crystals.

Step 4: Synthesis of 1,3-benzothiazol-2-yl(2-{[4-(morpholin-4-ylmethyl)benzyl]-oxy}pyrimidin-4-yl)acetonitrile (3)

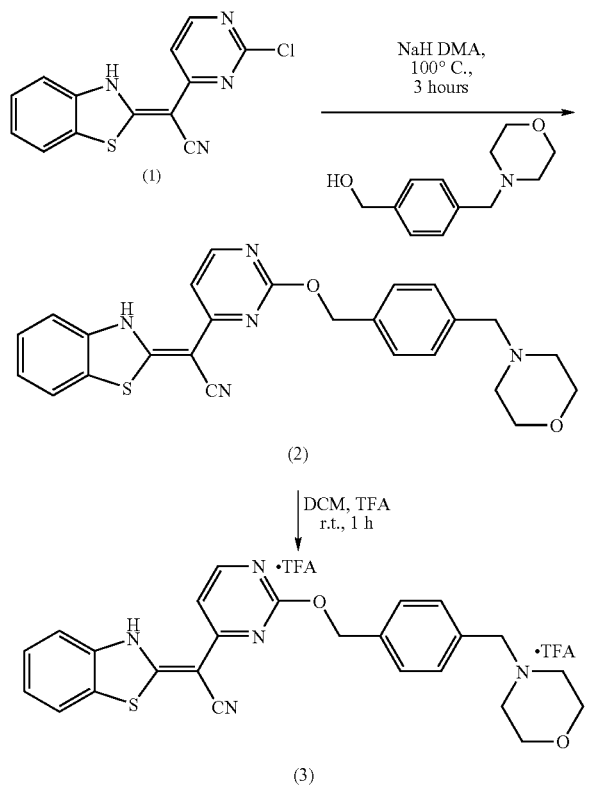

To a stirred suspension of NaH (60% in oil, 9.13 g, 0.21 mol, pre-washed with pentane) in dry DMA (300 ml), in a three-neck flask fitted with a mechanic stirrer, was added drop wise under inert atmosphere a solution of the N-(4-Hydroxymethylbenzyl-morpholine (21.7 g, 0.104 mol), in dry DMA (300 ml). After 1 h stirring at r.t, a suspension of (1) (15 g, 0.052 mol) in dry DMA (300 ml) was added dropwise. The reaction mixture was allowed to stir under inert atmosphere at 100° C. until complete disappearance of the starting material (3 hours). The reaction was quenched by addition of water and the mixture was evaporated to near dryness. Water/EtOAc (~10:1) were added. After one night in fridge, a fine precipitate was obtained. The product was obtained by centrifugation (15 min. and 3000 rpm/min) after removal of the supernatant. It was washed with water (3×), using centrifugation in the same conditions. The orange solid obtained was taken up in water then filtered off and washed with cyclohexane. HPLC (Conditions a, max plot): 95.8%, rt. 2.29 min.

The orange solid (2) was taken up in a mixture of DCM (300 ml)/TFA (50 ml). The yellow fluffy solid formed by addition of ether (600 ml) was filtered off, washed with ether (3×) then dried under vacuum at r.t, affording 20 g of diTFA salt. 12+g of the product were purified by preparative HPLC and the pure fractions obtained were lyophilized affording 11.4 g (53% from (1)) of di TFA salt as a bright yellow fluffy solid.

458.23 (M+1); HPLC (Conditions a, max plot): 99.5%, rt. 2.19 min $^1$HNMR (DMSO-d6) δ 10.22 (very br s, 1H) 7.93 (d, J=7.9 Hz, 1H), 7.89 (br d, 1H), 7.73 (d, J=7.9 Hz, 1H), 7.68-7.65 (m, 2H), 7.57-7.54 (m, 2H), 7.44-7.39 (m, 1H), 7.28-7.23 (m, 1H), 6.72 (br d, 1H), 5.73 (s, 2H), 4.38 (s, 2H), 4.04-3.78 (m, 2H), 3.74-3.47 (m, 2H), 3.32-3.02 (m, 4H)

CHN analysis: $C_{25}H_{23}N_5O_2S$. 2TFA: Calculated: C, 50.80%; H, 3.68%; N, 10.21%. Found: C, 50.07%; H, 4.04%; N, 10.21%.

The compounds of formula (I) may be subjected to the following Assays of Examples 2 to 5, in order to demonstrate their utility for the treatment of scleroderma and its therapeutic implications such as systemic sclerosis, scleroderma-like disorders or sine scleroderma.

Example 2

Determination of Bleomycin-Induced Body Weight Loss

The objective of the present Assay is to determine the loss of body weight of mice which is usually triggered by bleomycin-induced lung fibrosis.

Female 10- to 12-week-old C57BL/6 wild-type mice were intratracheally instilled with bleomycin (3.75 U/kg) dissolved in 10 μl saline to induce the fibrosis in the lungs. The treatment with a test compound started on day 0 and was continued daily—from day 0 (1 hour before the bleomycin instillation) to day 17. The test compound was administered orally at different dosages. Control mice were intratracheally instilled with saline on day 0. The body weight loss was recorded on a daily basis and the results of the determination are graphically represented in FIG. 1.

All bleomycin instilled mice showed a similar body weight loss until day 5 post-instillation in contrast to saline instilled mice (control) that had stable body weight. From day 5 to day 17, mice treated with a test compound showed stabilization of their body weight in contrast to saline-treated mice that continue to loose body weight with time until sacrifice on day 17. This is shown in an exemplary way in FIG. 1 for the specific test compound (A) (i.e. 1,3-benzothiazol-2-yl(2-{[4-(morpholin-4-ylmethyl)benzyl]-oxy}pyrimidin-4-yl)acetonitrile).

FIG. 1 shows a total of 4 curves, each curve representing an animal group treated under different conditions:

Curve with squares (n=10): mice treated with 2 mg/kg of test compound (A).

Curve with triangles (n=10): mice treated with 7 mg/kg of test compound (A).

Curve with lozenges (n=10): mice treated with saline alone.

Curve with filled circles: control mice, intratracheally instilled with saline on day 0.

FIG. 1 demonstrates that the loss of body weight induced by bleomycin in mice treated with the test compound (A) at day 17 is reduced by about 30% at a dosage of 2 mg/kg.

Example 3

Determination of Bleomycin-Induced Pulmonary Oedema

Lung fibrotic changes following instillation of bleomycin result from the infiltration of inflammatory cells like macrophages, lymphocytes and neutrophils into the lungs a well as an increase in pro-inflammatory cytokines such as TNFα. The pulmonary oedema is analyzed to determine whether a test compound affects the bleomycin-induced lung inflammation. What is determined is the difference wet/dry of the examined lungs, where high differences indicate a high degree of pulmonary oedema.

Mice were treated as described in Example 2. The test compound was compound (A) (i.e. 1,3-benzothiazol-2-yl(2-{[4-(morpholin-4-ylmethyl)benzyl]-oxy}pyrimidin-4-yl)aceto-nitrile). At day 17 of instillation, animals were euthanized and both lungs were removed. The right lungs of each mouse were resected, rinsed in 0.9% saline, blotted dry, trimmed free of heart and other extraneous tissue and weighed immediately before lyophilization followed by weighing. The lung dry and wet weight differences were calculated and graphically reported in FIG. 2. which illustrates the outcome of the assay for the test compound (A). The results are indicated as the mean values of seven mice in each group A to D. Each of the black columns A to D in FIG. 2 shows the dry/wet weight difference of lungs for the groups of animals A to D, treated under the following conditions:

Group A: mice instilled with saline.
Group B: mice instilled with bleomycin and orally treated with saline.
Group C: mice instilled with bleomycin and orally treated with 2 mg/kg test compound (A).
Group D: mice instilled with bleomycin and orally treated with 7 mg/kg test compound (A).

Figure 2:

From FIG. 2 it is concluded that a significant reduction in pulmonary oedema is observed in groups of mice treated with the test compound (A) at 2 and 7 mg/kg compared with saline-treated mice (statistical reproducibility $p=0.016$ and $p=0.009$ respectively).

Example 4

Determination of Bleomycin-Induced Pulmonary Fibrosis

Injection of bleomycin in mice induces focal fibrotic lesions with thickened intra-alveolar septa, collapse of alveolar septa as well as massive infiltration of lymphocytes into the lung interstitium. Such focal fibrotic lesions are histologically determined on day 17 after bleomycin administration.

Figure 3:

Mice were treated as described in Example 2. At day 17 of administration, the animals were euthanized, the right lungs of each mouse were resected, fixed in 10% formalin, embedded in paraffin, sectioned, stained with Masson's trichrome solution, and examined by light microscopy for histological changes. Morphological evaluation of bleomycin-induced lung inflammation and fibrosis was performed using a semi-quantitative scoring method consisting in a visual evaluation of histological section photos in which the surface of the fibrotic part of the lung is evaluated compared to the total surface. FIG. 3 illustrates the outcome of the assay for the test compound (A). The pathological scores, in the ordinate of FIG. 3, are defined as % of inflammation and fibrosis (lesions) of the lungs. Results are indicated, as the mean values of the pathological scores for three sections for individual mice and for seven mice in each group. Thus, each of the black columns in FIG. 3 shows the percentage of lesions in the lungs of the groups of animals A to D treated under the following conditions:

Group A: mice instilled with saline.
Group B: mice instilled with bleomycin and orally treated with saline.
Group C: mice instilled with bleomycin and orally treated with 2 mg/kg test compound (A).
Group D: mice instilled with bleomycin and orally treated with 7 mg/kg test compound (A).

As shown in FIG. 3, histological scoring of the fibrotic lesions shows that the treatment with test compound (A) at 7 and 20 mg/kg significantly reduced bleomycin-induced lung fibrosis compared with saline-treated mice, (statistical reproducibility $p=0.016$ and $p=0.009$, respectively).

Example 5

Determination of Bleomycin-Induced Lung Collagen Content

The objective of the present assay is to determine the reduction in lung fibrosis by specifically measuring the hydroxyproline content in the lungs of bleomycin-treated mice. Hydroxyproline is an amino acid component necessary for the build-up of collagen. The quantification of hydroxyproline in the lung after collagen hydrolysis is therefore seen as a suitable indicator for lung collagen content.

Figure 4:
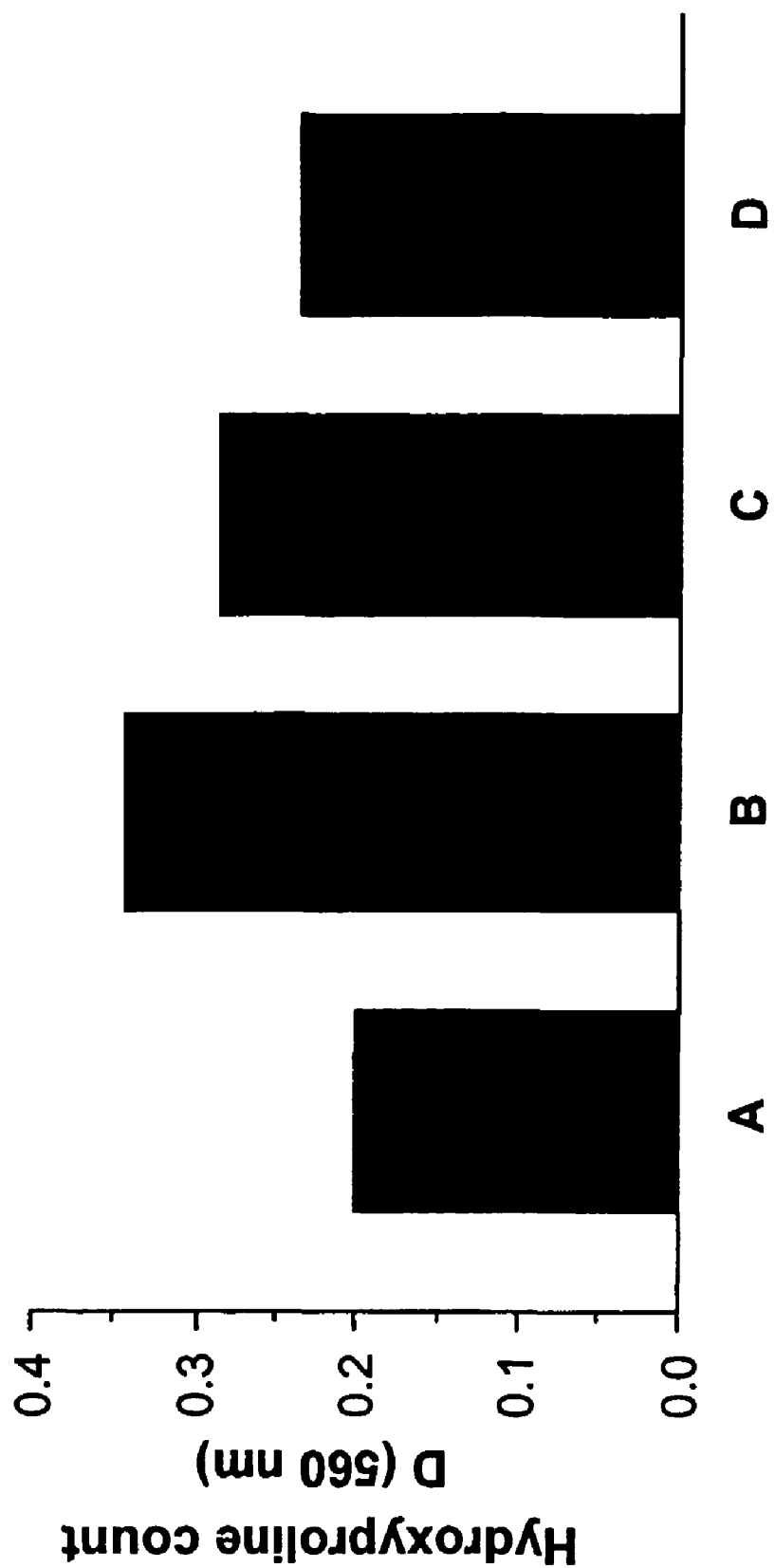

Mice were treated as described in Example 2. At day 17 of instillation, the animals were euthanized, and both lungs were removed. Total lung collagen was determined by analysis of hydroxyproline. Briefly, lungs were homogenized in Tris-HCl, pH 7.6, with a Tissue Tearor followed by incubation in Amberlite overnight at 115° C. Citrate/acetate buffer, isopropanol, chloramine-T and DAB solutions were added to the samples and left for 30 min at 60° C. Samples were cooled for 10 min and read at 560 nm on spectrophotometer. FIG. 4 illustrates the outcome of the assay for the test compound (A). Results are indicated in FIG. 4 as with twelve mice in each group. Each of the black columns in FIG. 4 shows the hydroxyproline count in the lungs of the groups of animals A to E treated under the following conditions:

Group A: mice instilled with saline.
Group B: mice instilled with bleomycin and orally treated with saline.
Group C: mice instilled with bleomycin and orally treated with 2 mg/kg test compound (A).
Group D: mice instilled with bleomycin and orally treated with 7 mg/kg test compound (A).

The hydroxyproline content in the lungs is determined on day 17 after the injection of bleomycin. It is found that the lung hydroxyproline content was significantly lower in mice treated with 7 mg/kg of test compound (A) compared with saline-treated mice (statistical reproducibility $p=0.009$).

Example 6

Preparation of a Pharmaceutical Formulation

The following formulation examples illustrate representative pharmaceutical compositions according to the present invention being not restricted thereto.

Formulation 1—Tablets

A benzazole compound of formula (I) is admixed as a dry powder with a dry gelatin binder in an approximate 1:2 weight ration. A minor amount of magnesium stearate is added as a lubricant. The mixture is formed into 240-270 mg tablets (80-90 mg of active benzazole compound per tablet) in a tablet press.

Formulation 2—Capsules

A benzazole compound of formula I is admixed as a dry powder with a starch diluent in an approximate 1:1 weight ratio. The mixture is filled into 250 mg capsules (125 mg of active benzazole compound per capsule).

Formulation 3—Liquid

A benzazole compound of formula I, sucrose and xanthan gum are blended, passed through a No. 10 mesh U.S. sieve, and then mixed with a previously prepared solution of microcrystalline cellulose and sodium carboxymethyl cellulose in water. Sodium benzoate, flavor, and color are diluted with water and added with stirring. Sufficient water is then added to produce a total volume of 5 mL.

Formulation 4—Tablets

A benzazole compound of formula I is admixed as a dry powder with a dry gelatin binder in an approximate 1:2 weight ratio. A minor amount of magnesium stearate is added as a lubricant. The mixture is formed into 450-900 mg tablets (150-300 mg of active benzazole compound) in a tablet press.

Formulation 5—Injection

A benzazole compound of formula I is dissolved in a buffered sterile saline injectable aqueous medium to a concentration of approximately 5 mg/ml.

REFERENCES

1. LeRoy, "Increased collagen synthesis by scleroderma skin fibroblasts in vitro" *J. Clin. Invest.* 54, p. 880-89 (1974)
2. Leighton, *Drugs* 61(3) p. 419-27 (2001)
3. Wigley and Sule, *Expert opinion on Investigational Drugs* 10(1) p. 3148 (2001)
4. *The EMBO Journal Vol.* 18 No. 5 p. 1345-56 (1999)
5. *Free Radical Biol. Med.*, 30(8), p. 846-57 (2001)
6. *Am. J. Physiol.*, 278(3, Pt. 1), C570-C581 (English) 2000
7. *PNAS, vol.* 97, p. 1778-83 (2000) by Kaminski et al.
8. WO 9855110
9. EP 110957.

The invention claimed is:

1. A method for treating interstitial pulmonary fibrosis, comprising administering to a patient in need thereof that is suffering from interstitial pulmonary fibrosis an effective amount of a benzothiazole according to formula I

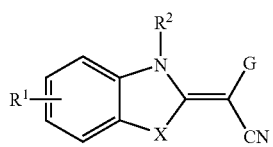

(I)

or its tautomers, its geometrical isomers, its optically active forms as enantiomers, diastereomers and its racemate forms, pharmaceutically acceptable salts thereof, and combinations thereof, wherein:

X is O, S or $NR^0$, with $R^0$ being H or an $C_1$-$C_6$ alkyl;
G is an pyrimidinyl group of the formula

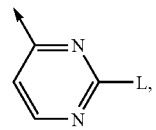

wherein L is selected from the group consisting of hydrogen, $C_1$-$C_6$ alkyl, $C_1$-$C_6$ alkoxy, $C_1$-$C_6$ thioalkoxy, $C_2$-$C_6$ alkenyl, $C_2$-$C_6$ alkynyl, primary, secondary or tertiary amino groups, aminoacyl, aminocarbonyl, amino-($C_1$-$C_{10}$)alkyl, amino-($C_1$-$C_{10}$)-alkyl-aryl, amino-($C_1$-$C_{10}$)alkyl-heteroaryl, $C_1$-$C_6$ alkoxycarbonyl, carboxyl, cyano, halogen, hydroxy, nitro, sulfoxy, sulfonyl, aryl, heteroaryl, 3-8 membered cycloalkyl, optionally containing at least one heteroatom selected from N, O, S, and hydrazido groups, wherein the arrow indicates the point of attachment;

$R^1$ is selected from the group consisting of hydrogen, $C_1$-$C_6$-alkoxy, $C_1$-$C_6$-thioalkoxy, $C_1$-$C_6$-alkyl, $C_2$-$C_6$-alkenyl, $C_2$-$C_6$-alkynyl, primary, secondary or tertiary amino groups, aminoacyl, aminocarbonyl, $C_1$-$C_6$ alkoxycarbonyl, aryl, heteroaryl, carboxyl, cyano, halogen, hydroxy, nitro, sulfoxy, sulfonyl, sulfonamide or hydrazides;

$R^2$ is selected from the group consisting of hydrogen, $C_1$-$C_6$-alkyl, $C_2$-$C_6$-alkenyl, $C_2$-$C_6$-alkynyl, $C_1$-$C_6$-alkyl-aryl, aryl or heteroaryl, $C_1$-$C_6$-alkyl-heteroaryl, —C(O)—OR$^3$, —C(O)—R$^3$, —C(O)—NR$^3$R$^{3'}$, —(SO$_2$)R$^3$, with $R^3$ and $R^{3'}$ being independently selected from the group consisting of hydrogen, $C_1$-$C_6$ alkyl, $C_2$-$C_6$ alkenyl, $C_2$-$C_6$ alkynyl, aryl, heteroaryl, $C_1$-$C_6$-alkyl aryl, $C_1$-$C_6$-alkyl heteroaryl.

2. The method of claim 1, wherein said benzothiazole is 1,3-benzothiazol-2-yl(2-{[4-(morpholin-4-ylmethyl)benzyl]oxy}pyrimidin-4-yl)-acetonitrile.

3. The method of claim 1, wherein $R^1$ is selected from the group consisting of hydrogen, halogen, $C_1$-$C_6$ alkyl or $C_1$-$C_6$ alkoxy.

4. The method of claim 1, wherein the benzothiazole is its tautomer according to formula II

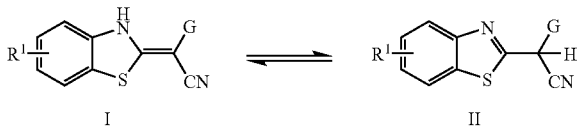

or its geometrical isomers, its optically active forms as enantiomers, diastereomers and racemate forms, pharmaceutically acceptable salts thereof, and combinations thereof, wherein G is a pyrimidinyl group of the formula

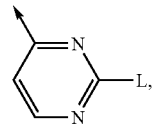

wherein L is selected from the group consisting of hydrogen, $C_1$-$C_6$ alkyl, $C_1$-$C_6$ alkoxy, $C_1$-$C_6$ thioalkoxy, $C_2$-$C_6$ alkenyl, $C_2$-$C_6$ alkynyl, primary, secondary or tertiary amino groups, aminoacyl, aminocarbonyl, amino-($C_1$-$C_{10}$)alkyl, amino-($C_1$-$C_{10}$)-alkyl-aryl, amino-($C_1$-$C_{10}$)alkyl-heteroaryl, $C_1$-$C_6$ alkoxycarbonyl, carboxyl, cyano, halogen, hydroxy, nitro, sulfoxy, sulfonyl, aryl, heteroaryl, 3-8 membered cycloalkyl, optionally containing at least one heteroatom selected from N, O, S, and hydrazido groups wherein the arrow indicates the point of attachment; and $R^1$ is selected from the group consisting of hydrogen, $C_1$-$C_6$-alkoxy, $C_1$-$C_6$-thioalkoxy, $C_1$-$C_6$-alkyl, $C_2$-$C_6$-alkenyl, $C_2$-$C_6$-alkynyl, primary, secondary or tertiary amino groups, aminoacyl, aminocarbonyl, $C_1$-$C_6$ alkoxycarbonyl, aryl, heteroaryl, carboxyl, cyano, halogen, hydroxy, nitro, sulfoxy, sulfonyl, sulfonamide, hydrazides.

5. The method of claim 1 or 4, wherein L is a group —N($R^a$, $R^b$) or —O$R^a$, with $R^a$ and $R^b$ being each independently selected from the group consisting of H, ($C_1$-$C_{10}$)-alkyl, $C_1$-$C_6$ alkyl-aryl, $C_1$-$C_6$-alkyl-heteroaryl, aryl or heteroaryl and 4-8 membered saturated or unsaturated cycloalkyl.

6. The method of claim 5, wherein L is selected from the group consisting of:

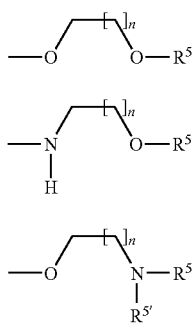

wherein n is 1 to 10, and $R^5$ and $R^{5'}$ are independently selected from each other from the group consisting of H, $C_1$-$C_{10}$ alkyl, aryl or heteroaryl, $C_1$-$C_6$ alkyl-aryl and $C_1$-$C_6$-alkyl-heteroaryl.

7. The method of claim 6, wherein n is 1 to 6.

8. The method of claim 6, wherein X is S, $R^1$ and $R^2$ are H or $C_1$-$C_6$ alkyl, G is a pyrimidinyl group

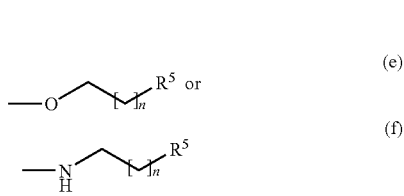

with L being either (e), (f)

wherein n is 0, 1 or 2 and $R^5$ is an aryl or heteroaryl.

9. The method of claim 8, wherein $R^5$ is phenyl, pyridyl or imidazolyl.

* * * * *